United States Patent [19]

Wong

[11] Patent Number: 5,335,534

[45] Date of Patent: Aug. 9, 1994

[54] FUNCTIONAL TESTING METHOD FOR TOXIC GAS SENSORS

[75] Inventor: Jacob Y. Wong, Santa Barbara, Calif.

[73] Assignee: Gaztech International Corporation, Goleta, Calif.

[21] Appl. No.: 894,919

[22] Filed: Jun. 8, 1992

[51] Int. Cl.$^5$ .................. G01N 21/35; G01C 25/00; G01D 18/00; G12B 13/00

[52] U.S. Cl. .................. 73/1 G; 250/252.1; 250/363.09; 436/9

[58] Field of Search .............. 73/1 G; 436/9; 250/252.1, 363.09

[56] References Cited

U.S. PATENT DOCUMENTS

| | | | |
|---|---|---|---|
| 3,844,905 | 10/1974 | Epstein et al. | 73/1 G |
| 4,053,785 | 10/1977 | Lee et al. | 250/252.1 A |
| 4,673,812 | 6/1987 | Yoneda | 250/252.1 A |
| 4,687,934 | 8/1987 | Passaro et al. | 250/252.1 A |
| 4,801,804 | 1/1989 | Rosenthal | 250/252.1 A |
| 5,060,505 | 10/1991 | Tury et al. | 73/1 G |
| 5,184,017 | 2/1993 | Tury et al. | 250/252.1 A |
| 5,204,532 | 4/1993 | Rosenthal | 250/252.1 A |
| 5,206,511 | 4/1993 | Apperson et al. | 250/252.1 A |

Primary Examiner—Hezron E. Williams
Assistant Examiner—George Dombroske
Attorney, Agent, or Firm—Daniel C. McKown

[57] ABSTRACT

The proper operation of an NDIR toxic gas sensor can be checked by using a non-toxic gas that has an absorption band that overlaps the absorption band used for measuring the toxic gas. The NDIR sensor cannot distinguish which of the two gases is responsible for causing the observed absorption of radiation in the sensor. Since detectors of toxic gases typically operate at low concentration levels, the extent of overlap between the absorption band of the toxic gas and of the non-toxic gas may be relatively small, since a larger concentration of the non-toxic gas can be used with no ill effects. The method may be applied to sensors for detecting carbon monoxide or methane for example.

2 Claims, 1 Drawing Sheet

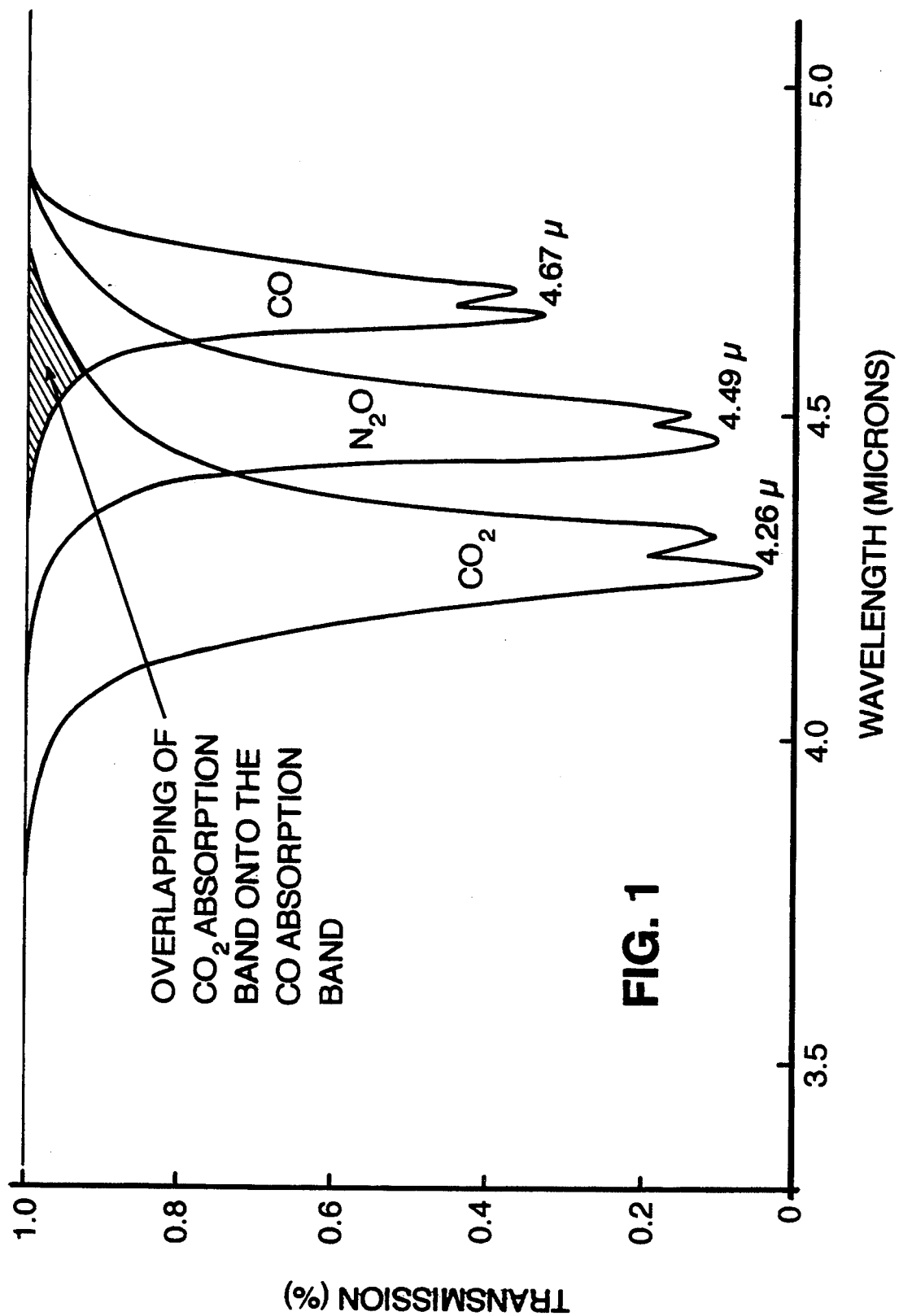

FUNCTIONAL TESTING METHOD FOR TOXIC GAS SENSORS

BACKGROUND OF THE INVENTION

Field of the Invention

The present invention relates to a method for determining whether a toxic gas sensor is functioning properly at any particular time. Surprisingly, no toxic gas is needed to perform the test.

Toxic gas sensors are widely used for sensing a build-up in the concentration of a toxic gas, for example, carbon monoxide, methane, hydrogen sulfide, and others, to protect the lives of persons who are exposed to the toxic gas. It is essential that the toxic gas sensor operate reliably, and to this end it is desirable to test the operation of the sensor from time to time.

At the completion of the manufacturing process, the sensor is calibrated by exposing it to an accurately controlled concentration of the toxic gas and noting the output reading of the sensor. At this point there is no doubt that the sensor is functioning properly and can be depended upon to save lives.

Thereafter, the sensor is transported, handled, and put into daily use where it is exposed to a number of environmental stresses. After a period of such use, the sensors may be found to have changed due to aging, due to chemical reactions with environmental elements such as moisture, particulates, smoke, various gases, insects, soot, and oil vapors, and due to chemical instabilities. In most instances, these environmental stresses affect the functioning and sensitivity of the sensors. If the sensor ceases to operate continuously, or if its sensitivity becomes sufficiently degraded, the sensor can no longer be relied on to protect the lives of those who are depending on it. Thus, it is seen to be highly desirable to provide a simple and easy method for testing the toxic gas sensors from time to time, to assure that they are continuing to operate properly.

Initially, one might consider the possibility of providing to the users of the sensors actual samples of the toxic gases for performing this periodic testing. However, upon further consideration this does not seem to be a good solution because frequently the users of the sensors are not familiar with proper techniques for handling the toxic gases, and they normally would not have appropriate apparatus for handling the toxic gases, so that there would be a large risk involved. Of course, some toxic gases are more deadly than others, but an element of risk still remains.

The present invention is directed to a method for testing the operation of a toxic gas sensor without using any toxic gas.

SUMMARY OF THE INVENTION

Each toxic gas has absorption bands at characteristic wavelengths in which the toxic gas absorbs radiation. Normally those absorption bands lie in the infrared portion of the electromagnetic spectrum. Because the bands are related to the molecular structure of the gas is characterized by its own own peculiar set of absorption bands. A well known technique for detection of a gas is to monitor the absorption of radiation by one of its absorption bands. When the gas to be detected is present, some of the radiation is absorbed. The absorption is measured and is related to the concentration of the gas. This is called the NDIR (Non-Dispersive InfraRed) technique.

Although the set of absorption bands belonging to a particular gas is unique, it is not unusual for a few of the spectral bands for different gases to overlap. Ordinarily, such overlapping is considered undesirable because if the measurement is carried out in such an overlapping band, it is not clear which of several gases produced the observed absorption. This problem is referred to as interference or non-specificity.

For example, carbon monoxide (CO) has an absorption band centered at 4.67 microns in the infrared portion of the spectrum. Using standard NDIR technique, one can devise a CO sensor using this particular absorption band. However, carbon dioxide ($CO_2$) has a very strong absorption band centered at 4.26 microns which slightly overlaps the 4.67 micron band of carbon monoxide. Further, nitrous oxide ($N_2O$) also has a very strong absorption band at 4.49 microns. FIG. 1 depicts these three absorption bands.

Thus, an NDIR sensor devised for detecting carbon monoxide by using the 4.67 absorption band of carbon monoxide may yield erroneous results unless special precautions are taken. It is well known that carbon dioxide gas is present in the atmosphere, typically in concentrations as great as several thousand parts per million. Unless special precautions are taken to keep carbon dioxide out of the sample chamber, the attempted measurement of carbon monoxide may be inaccurate. On the other hand, nitrous oxide $N_2O$ gas is present in the atmosphere only in trace quantities and for many purposes this would not be a problem.

Ordinarily, the presence of an interfering gas requires the addition of a reference channel to the sensor so as to compensate the readings for the presence of the interfering gas.

The present inventor has turned this overlapping of spectral bands, normally considered disadvantageous, into a very helpful technique for checking the operation of an NDIR sensor to assure that it is operating properly.

The novel features which are believed to be characteristic of the invention, both as to organization and method of operation, together with further objects and advantages thereof, will be better understood from the following description in which a preferred embodiment of the invention is described by way of example. It is to be expressly understood, however, that the example is for the purpose of illustration and description only and is not intended as a definition of the limits of the invention.

BRIEF DESCRIPTION OF THE DRAWINGS

FIG. 1 is a graph showing the absorption spectra of carbon monoxide, carbon dioxide, and nitrous oxide versus wavelength.

DETAILED DESCRIPTION OF THE PREFERRED EMBODIMENT

The present invention is based on the fact that the detector of an NDIR instrument responds to the total radiation falling upon it. The instrument registers the total amount of absorption that has occurred, but it cannot tell which of two interfering gases caused an observed absorption.

Fortunately, the present inventor has been able to turn this fact into an advantage when the operation of a toxic gas sensor is to be checked. It is necessary first to find a non-toxic gas that interferes with the toxic gas to be measured by having an absorption band that overlaps the absorption band of the toxic gas.

Next, it is necessary to determine experimentally the concentration of the non-toxic gas required to produce the same amount of absorption as produced by a specified concentration of the toxic gas.

Thereafter, when the operation of the sensor is to be tested, it is necessary only to use the non-toxic gas in the appropriate concentration. It produces a response equivalent to that produced by the specified concentration of the toxic gas. In the process, all of the functioning electronics, optics, infrared source, detector, and even the calibration of the sensor are tested.

For example, if one wishes to measure the concentration of the toxic gas carbon monoxide (CO), one could find from a handbook that carbon dioxide has an absorption band centered at 4.26 microns that partially overlaps the 4.67 micron absorption band of carbon monoxide.

One could also find from a handbook that nitrogen gas ($N_2$) has no absorption band that overlaps the 4.67 micron band of carbon monoxide. Therefore, one could mix carbon dioxide gas with nitrogen gas to produce a non-toxic testing sample.

Assuming, by way of example, that the interference of carbon dioxide gas on the carbon monoxide absorption band being detected is such that for every 100 parts per million (ppm) of carbon dioxide the instrument registers four parts per million of carbon monoxide gas. In this case one can use 25,000 parts per million of carbon dioxide gas (in nitrogen) to test the response of a sample having a concentration of 1,000 parts per million of carbon monoxide. If one passes the 25,000 ppm $CO_2$ gas through the CO sensor and the latter registers correctly 1,000 ppm of CO, then one can rest assured that the CO sensor is functioning properly at a concentration level of 1,000 ppm of CO gas. Thus, a safe gas (carbon dioxide) can be used to test the proper operation of a toxic gas (carbon monoxide) sensor without resorting to the use of the toxic gas itself.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A method of testing a toxic gas sensor, said toxic gas sensor being of a type in which the absorption of radiation is monitored in an absorption band peculiar to the toxic gas and in which the presence of the toxic gas is indicated by an increase in absorption of the radiation, said method comprising the steps of:

applying to said sensor a sample of a non-toxic gas, said sample known to contain none of the toxic gas, said sample including a gas that absorbs radiation, to a known extent, in the absorption band peculiar to the toxic gas; and, comparing the absorption produced by the sample of a non-toxic gas with the absorption produced by a sample of the same non-toxic gas at an earlier time when the toxic gas sensor was known to have been operating satisfactorily.

2. A method of testing a toxic gas sensor, said toxic gas sensor being of a type in which the absorption of radiation is monitored in an absorption band peculiar to the toxic gas and in which the presence of the toxic gas is indicated by an increase in absorption of the radiation, said method comprising the steps of:

a) calibrating the toxic gas sensor by applying to it a sample of the toxic gas in a preselected concentration and noting the absorption;

b) as soon as possible after step a), applying to said toxic gas sensor a sample of a non-toxic gas, said sample known to contain none of the toxic gas, said sample of a non-toxic gas including a gas that absorbs radiation, to a known extent, in the absorption band peculiar to the toxic gas, and noting the absorption;

c) repeating step b) at a later time using a non-toxic gas of identical composition to that used in step b); and, d) comparing the absorption measured in step c) with the absorption measured in step b), whereby, to the extent that the measured absorptions agree, the toxic gas sensor is functioning satisfactorily.

* * * * *